(12) United States Patent
Fernandez et al.

(10) Patent No.: US 11,634,757 B2
(45) Date of Patent: Apr. 25, 2023

(54) EMULSIONS WITH IMPROVED STABILITY

(71) Applicant: Stilla Technologies, Villejuif (FR)

(72) Inventors: Nicolas Fernandez, Paris (FR); Étienne Fradet, Arcueil (FR); Rémi Dangla, Paris (FR)

(73) Assignee: STILLA TECHNOLOGIES, Villejuif (FR)

( * ) Notice: Subject to any disclaimer, the term of this patent is extended or adjusted under 35 U.S.C. 154(b) by 162 days.

(21) Appl. No.: 16/757,295

(22) PCT Filed: Oct. 19, 2018

(86) PCT No.: PCT/EP2018/078726
§ 371 (c)(1),
(2) Date: Apr. 17, 2020

(87) PCT Pub. No.: WO2019/077114
PCT Pub. Date: Apr. 25, 2019

(65) Prior Publication Data
US 2021/0189476 A1   Jun. 24, 2021

Related U.S. Application Data

(60) Provisional application No. 62/575,698, filed on Oct. 23, 2017.

(30) Foreign Application Priority Data

Oct. 20, 2017   (EP) .................................... 17306437

(51) Int. Cl.
| C12Q 1/68 | (2018.01) |
| B01L 3/00 | (2006.01) |
| C12Q 1/6848 | (2018.01) |
| C12Q 1/686 | (2018.01) |
| C09K 23/00 | (2022.01) |

(52) U.S. Cl.
CPC ...... *C12Q 1/6848* (2013.01); *B01L 3/502784* (2013.01); *C09K 23/00* (2022.01); *C12Q 1/686* (2013.01)

(58) Field of Classification Search
CPC ... C12Q 1/6848; C12Q 1/686; B01F 17/0057; B01L 3/502784; C09K 23/00
See application file for complete search history.

(56) References Cited

U.S. PATENT DOCUMENTS

| 4,683,195 A | 7/1987 | Mullis et al. |
| 4,683,202 A | 7/1987 | Mullis |
| 2011/0086352 A1 | 4/2011 | Bashir et al. |
| 2011/0159499 A1 | 6/2011 | Hindson et al. |
| 2011/0186784 A9 | 8/2011 | Bryning |
| 2015/0267242 A1 | 9/2015 | Foegeding et al. |
| 2015/0267246 A1 | 9/2015 | Baroud et al. |

FOREIGN PATENT DOCUMENTS

| CN | 207944100 U | 10/2018 |
| EP | 2315629 A1 | 5/2011 |
| EP | 2903738 A1 | 8/2015 |
| WO | 1999002671 A1 | 1/1999 |
| WO | 2010009365 A1 | 1/2010 |
| WO | 2012109600 A2 | 8/2012 |
| WO | 2012109600 A3 | 11/2013 |
| WO | 2014056930 A1 | 4/2014 |

OTHER PUBLICATIONS

Balasubramanian, A. et al. (2012, e-pub. Jan. 28, 2012). "Removal of Phenolic Compounds From Aqueous Solutions by Emulsion Liquid Membrane Containing Ionic Liquid [BMIM]+[PF6]- in Tributyl Phosphate," Desalination 289:27-34.
Barikbin, Z. (2013). "Droplet Microfluidics With Ionic Liquids For Chemical Analysis and Separations," Thesis—Univ. Singapore, 236 pages.
International Preliminary Report on Patentability dated Apr. 21, 2020, for PCT Application No. PCT/EP2018/078726, 7 pages.
International Search Report and Written Opinion, dated Jan. 10, 2019, for PCT Application No. PCT/EP2018/078726, 10 pages.

(Continued)

*Primary Examiner* — Jezia Riley
(74) *Attorney, Agent, or Firm* — Morrison & Foerster LLP (57) ABSTRACT

The present invention relates to an emulsion, preferably a water-in-oil emulsion. comprising: a continuous phase comprising a conductivity improving compound, a dispersed phase suspended in the continuous phase, and a surfactant. The present invention also relates to a population of droplets comprising an aqueous phase, dispersed in a continuous oily phase comprising an oil and a conductivity-improving compound. The present invention also relates to a microfluidic chip comprising a hydrophobic composition comprising an oil, a surfactant and a conductivity improving compound in an injection chamber configured so that injecting a hydroplilic composition through said injection means will generate an emulsion in the injection chamber; and to a kit comprising a microfluidic chip and a container comprising an aqueous composition. The present invention also relates to a process for manufacturing an emulsion according to the invention. The present invention also provides methods for analyzing biological material, for example for analyzing biological material within the emulsion of the invention.

16 Claims, 3 Drawing Sheets

(56) References Cited

OTHER PUBLICATIONS

Kong, Y. et al. (2015). "Study of Miniemulsion Formulation Containing 1-Octyl-3-Methylimidazolium Hexafluorophosphate for its Application in Low-Emitting Coating Products," Soft Matter 11(7):1293-1302.

Kong, Y. et al. (2016, e-pub. Dec. 19, 2015). "Effect of Ionic Liquids on Stability of O/W Miniemulsion for Application of Low Emission Coating Products," Chinese J. Chem. Eng. 24(1):196-201.

Teh, S.-Y et al. (Feb. 2008). "Droplet Microfluidics," Lab Chip. 8(2):198-220.

EMULSIONS WITH IMPROVED STABILITY

CROSS REFERENCE TO RELATED APPLICATIONS

This application is a National Phase application under 35 U.S.C. § 371 of International Application No. PCT/EP2018/078726, filed Oct. 19, 2018, which claims priority to European Application No. 17306437.9, filed Oct. 20, 2017, and U.S. Provisional Application No. 62/575,698, filed Oct. 23, 2017, the contents of each of which are incorporated herein by reference in their entirety.

FIELD OF INVENTION

The present invention pertains to the field of materials for analytical methods, and relates to an emulsion comprising at least one stability-improving compound, especially a compound for avoiding and/or reducing electro-coalescence of the emulsion.

The present invention also relates to a method using an emulsion comprising at least one stability-improving compound to perform a chemical and/or biological reaction, especially a polymerase chain reaction (PCR).

The present invention is especially useful for digital polymerase chain reaction (ddPCR™) methods.

BACKGROUND OF INVENTION

Emulsions are used in various chemical, industrial and analytical processes, and may typically comprise an aqueous dispersed phase suspended in an oily continuous phase (corresponding to water-in-oil emulsions), the suspension being stabilized by means of a surfactant or emulsifying agent.

Microfluidic devices have been recently developed to create emulsions under controlled conditions, and allow the production of monodisperse emulsion and the control of the content of each droplet in the emulsion. Different types of microfluidic devices for the creation of droplets have been described including co-flow, T-junction and flow-focusing microfluidic geometries, which use a flow of continuous phase to shear droplets from a stream of the dispersed phase in a junction between one or more channels that guide the flow of continuous phase and one or more channels that guide the flow of the dispersed phase.

It is also possible to create droplets using confinement gradients, a method in which the geometry of the microfluidic device, coupled with the surface tension that applies at the interface between the continuous phase and the dispersed phase, is driving the creation and flow of droplets. The key feature in such microfluidic devices is a sloped region on the side of a microfluidic chamber where the height of the chamber is thinnest at the rim of the chamber and increases linearly inwards. When the dispersed phase is fed into such a chamber filled with the continuous phase through this sloped region, the dispersed phase spontaneously breaks up into monodisperse droplets, provided that the dispersed phase does not wet the substrate of the microfluidic device.

For many applications, it is important that the emulsion remains stable after its manufacture, i.e., that the individual droplets of dispersed phase do not merge or coalesce spontaneously, neither under external stimuli. Especially, electric fields can destabilize emulsions, an effect known as electrocoalescence. Electro-coalescence events can lead to a localized coalescence of a small number of droplets within the emulsion but in some cases, it can also lead to large-scale coalescence of significant portions of the emulsion. These large-scale events can destroy substantial part of the emulsion, up to 75% or more of the emulsion.

Increasing the amount of surfactant or emulsifying agent within the emulsion may help to reduce the occurrence of electro-coalescence. However, doing so increases the manufacturing cost and renders the emulsion unsuitable for many specific uses, especially in the field of medicine or analysis. Moreover, electro-coalescence can occur even in the presence of surfactants that are usually considered as excellent stabilizing agents for emulsions. In some applications, it is required that the emulsion remains stable throughout a process, process which can include one or more step of directly or indirectly handling the emulsion. Therefore, there is still a need for improved emulsions wherein occurrence of electro-coalescence is controlled and/or suppressed.

Droplet digital PCR is one example of such a process. In droplet Digital™ PCR (ddPCR™), an aqueous mixture containing PCR reagents and genetic material to be analyzed is partitioned into microdroplets suspended in an oil comprising a surfactant using a microfluidic device, thereby creating a water-in-oil emulsion. Once created, the emulsion is collected from the microfluidic device using a manual or automated pipetting system and transferred onto a microtiter plate. The emulsion is then thermocycled by placing the microtiter plate on a standard thermocycler to amplify the genetic material contained in each droplet by PCR. After PCR, amplification products are detected in each droplet of the emulsion by flowing the emulsion through a second microfluidic channel in which droplets separate one from another and successively pass in front of an optical detector. In this example, the emulsion is manipulated multiple times, either directly when pipetted from the first microfluidic device to the microtiter plate or when extracted from the microtiter plate and into the optical detector, and indirectly as the microtiter plate loaded with the emulsion is transferred from instrument to instrument. In the literature, the process is described using a fluorinated oil (3M Novec HFE-7500) and a biocompatible fluoro-surfactant (PFPE-PEG-PFPE tri-block surfactant) as a surfactant to stabilize the droplets, as well as using mineral oil and. Span 80 as a surfactant.

Crystal Digital™ PCR (cdPCR™) is another example. In crystal Digital™ PCR, an aqueous mixture containing PCR reagents and genetic material to be analyzed is partitioned into a large 2D array of microdroplets inside an oil-filled microchamber of a microfluidic device. The 2D emulsion, also called a droplet crystal, remains in the microchamber throughout the crystal digital PCR process. After production of the droplet crystal, the emulsion is thermocycled within the microfluidic device using a flat-block thermocycler. After PCR, amplification products are detected in each droplet of the 2D emulsion by transferring the microfluidic device onto an imaging instrument which scans and images the droplet crystal within the microchamber through the transparent bottom part of the microfluidic device. In this example, the emulsion is indirectly manipulated as the microfluidic device is transferred from the thermocycler to the imaging instrument. The emulsion can also be indirectly manipulated when the microfluidic device is cleaned to remove dust particles and other smears or dirt marks from the bottom of the microfluidic device that may create optical artifacts when the droplet crystal is imaged.

In these two examples, droplets that coalesce or merge before the optical readout step cannot be taken into account in the analysis. Consequently, it is paramount to limit coalescence events in order to ensure precise and reliable analysis.

One source of uncontrolled and unwanted droplet coalescence is electrocoalescence. Electro-coalescence can be triggered by static electric that may build up on the microfluidic device, on the microtiter plates, on micropipettes or any other lab equipment used in the process, on the lab bench or on the hand gloves of the operator. Electro-coalescence can be triggered when the emulsion passes through the electric field generated by static electricity or when there is a discharge of static electricity from the container of the emulsion and onto another object, or vice versa.

Because it is difficult to control and/or suppress the build-up of static electricity in the environment in which may be handled an emulsion, it may be desirable to reduce the sensitivity of an emulsion to electric fields and electric discharges, in particular using compounds in the continuous phase.

Using an emulsion of the present invention to perform a biological reaction such as the amplification of a genetic element introduces an additional constraint on the choice of the compounds that may be added in the continuous phase. Especially, the compounds must not interfere negatively with the biological reaction.

Therefore, there is still a specific need for emulsions comprising a fluorinated oil as continuous phase, wherein occurrence of electro-coalescence is controlled and/or suppressed. There is also an unmet specific need for "biocompatible" emulsions for use in analytical methods such as ddPCR™ or cdPCR™, wherein occurrence of electro-coalescence is controlled and/or suppressed.

The Applicant conducted in-depth analysis of the phenomena of electro-coalescence and found that the inclusion of a conductivity-improving compound in the continuous phase of an emulsion could help to control and/or suppress electro-coalescence.

However, inclusion of a conductivity-improving compound in emulsions wherein the continuous phase is a fluorinated oil, such as ddPCR™ or cdPCR™ media, was especially difficult, because the conductivity-improving compound should be soluble in the fluorinated oil so that the continuous oily phase be under the form of a solution. The Applicant conducted further in-depth research and found that ionic compounds and especially ionic liquids could be used as conductivity-improving compound within a fluorinated oil wherein they are miscible.

Barikbin Z. ("Droplet Microfluidics with ionic liquids for chemical analysis and separation"—2013) discloses emulsions wherein the aqueous droplets are dispersed in silicon oil or fluorinated oil, the aqueous droplets being fully or partially engulfed in ionic liquid droplets. In other words, the ionic liquid is not miscible with the oily phase in these emulsions. In the work of Barikbin Z., avoiding coalescence was not an issue since the droplets are circulating in a microfluidic device during the whole process, thus not prone to coalescence.

US2011/086352 discloses methods and devices for microfluidic droplet PCR with electrical detection. In this system, PCR is performed in aqueous droplets circulating in a microfluidic device. It involves the use of aqueous droplets dispersed in a continuous phase being either mineral oil or an ionic liquid. No fluorinated oil is used in this system and when an ionic liquid is used, it is never suggested that it may be mixed with an oily phase. Moreover, coalescence was not an issue since the droplets are circulating.

WO2010/009365 discloses droplet libraries that may be used in microfluidic droplet PCR. Especially the disclosed water-in-oil emulsion libraries comprise a fluorinated oil as continuous phase, in which an aqueous phase is dispersed in presence of a fluorinated surfactant. There is no reference made to a possible use of an ionic liquid. As in above systems, coalescence was not an issue since the droplets are circulating in the PCR microfluidic device.

As previously mentioned, for bioanalytical applications such as ddPCR™ or cdPCR™, the conductivity-improving compound should not interfere with the biological assay, especially should not degrade the analyzed biological material. Therefore, prevention of electrocoalescence in ddPCR™ or cdPCR™ media was especially challenging. The Applicant further conducted in-depth research and found that specific biocompatible ionic liquids could be used as conductivity-improving compound within a fluorinated oil.

SUMMARY

The present invention relates to an emulsion comprising:
a continuous oily phase which is a solution comprising a fluorinated oil and a conductivity-improving compound,
a dispersed aqueous phase dispersed in said continuous oily phase, and
a fluorinated surfactant.

In one embodiment, the fluorinated surfactant is selected from perfluoro-octanol; 1H,1H,2H,2H-perfluoro-1-octanol; perfluoro-decanol; 1H,1H,2H,2H-perfluoro-1-decanol; perfluoro-tetradecanoic acid; perfluoro-tetradecanoic oligo ethylene glycol; perfluoropolyether; perfluoropolyether-polyethylene glycol; perfluoropolyether-polyethylene glycol-perfluoropolyether; perfluoropolyether-dimorpholinophosphate; polyhexafluoropropylene oxide carboxylate; polyhexafluoropropylene oxide-polyethylene glycol-polyhexafluoropropylene oxide; polyhexafluoropropylene oxide-polyether-polyhexafluoropropylene oxide; polyhexafluoropropylene oxide-polypropylene glycol-polyethylene glycol-polypropylene glycol-polyhexafluoropropylene oxide and mixtures thereof. In a more preferred embodiment, the fluorinated surfactant is polyhexafluoropropylene oxide-polyethylene glycol-polyhexafluoropropylene oxide or polyhexafluoropropylene oxide-polypropylene glycol-polyethylene glycol-polypropylene glycol-polyhexafluoropropylene oxide.

The present invention also relates to a population of droplets, comprising:
an aqueous phase, dispersed in,
a continuous oily phase which is a solution comprising a fluorinated oil and a conductivity-improving compound.

In one embodiment, the fluorinated oil is selected from perfluoro-hexane; perfluoro-cyclohexane; perfluoro-decaline; perfluoro-perhydrophenantrene; poly-hexafluoropropylene oxide such as poly-hexafluoropropylene oxide with carboxylic end group; perfluoro polytrimethylene ether; poly perfluoroalkylene oxide; fluorinated amines such as N-bis(perfluorobutyl)N-trifluoromethyl amine, tri(perfluoropentyl)amine, mixture of perfluorooctane amine and perfluoro-1-oxacyclooctane amine, perfluorotripropylamine; fluorinated ethers such as mixture of methyl nonafluorobutyl ether and methyl nonafluoroisobutyl ether, 3-ethoxy-1,1,1,2,3,4,4,5,5,6,6,6-dodecafluoro-2-(trifluoromethyl)-hexane, 2,3,3,4,4-pentafluorotetrahydro-5-methoxy-2,5-bis[1,2,2,2-tetrafluoro-1-trifluoromethyl) ethyl]-furan; and mixtures thereof. In a more preferred embodiment, the fluorinated oil is 3-ethoxy-1,1,1,2,3,4,4,5,5,6,6,6-dodecafluoro-2-(trifluoromethyl)-hexane.

In one embodiment, the conductivity-improving compound is an ionic compound. In one embodiment, the conductivity-improving compound is an ionic liquid. In one embodiment, the ionic compound or the ionic liquid comprises a fluorinated anion and/or a fluorinated cation. In a preferred embodiment, the ionic compound or the ionic liquid comprises a fluorinated anion. In a more preferred embodiment, the ionic compound or the ionic liquid comprises bis(trifluoromethanesulfonyl)imide.

In one embodiment, the ionic liquid is selected from N-trimethyl-N-butylammonium bis(trifluoromethanesulfonyl)imide 1-butyl-1-methylpyrrolidinium bis(trifluoromethanesulfonyl)imide, 1-ethyl-3-methylimidazolium bis(trifluoromethylsulfonyl)imide, 1-hexyl-3-methylimidazolium tris(pentafluoroethyl)trifluorophosphate, 2,3-dimethylimidazolium tetracyanoborate, N-tributyl-N-methylammonium bis(trifluoromethanesulfonyl)imide, and mixtures thereof. In one embodiment, the ionic liquid is N-tributyl-N-methylammonium bis(trifluoromethanesulfonyl)imide.

In one embodiment, the aqueous phase comprises biological material and/or reagents for performing a chemical and/or biological reaction. In a preferred embodiment, the aqueous phase comprises nucleic acid template and/or reagents for performing a chemical and/or biological reaction.

In one embodiment, each droplet in the population of droplets comprises a nucleic acid template and at least one pair of oligonucleotide primers being specific for a target nucleic acid sequence.

The present invention also relates to a microfluidic device comprising:
- a microchannel,
- a droplet generator means, and
- an emulsion or a population of droplets according to the present invention.

The present invention also relates to a method for analyzing a biological material, comprising:
- forming an emulsion or a population of droplets according to the present invention,
- processing said biological material in said emulsion or population of droplets, and
- detecting said biological material in said emulsion or population of droplets.

In one embodiment, the biological material is cells or nucleic acids.

In one embodiment, the step of processing of the biological material comprises amplifying the biological material. In a preferred embodiment, the step of processing of the biological material comprises amplifying the biological material by PCR. In a more preferred embodiment, the step of processing of the biological material comprises amplifying the biological material by droplet digital PCR (ddPCR).

Definitions

In the present invention, the following terms have the following meanings:

"About" preceding a figure means plus or less 10% of the value of said figure.

"Aqueous composition" refers to a composition which comprises water.

"Aqueous phase" refers to a phase of an emulsion which comprises water. In the emulsion according to the invention, aqueous phase is typically more hydrophilic than the other phase of the emulsion, which is relatively more hydrophobic.

"Biocompatible" refers to a material, substance, composition, compound, molecule, polymer or system which does not interfere with a biological assay and/or does not degrade a biological material.

"Biological material" refers, without limitation, to organisms, organs, tissues, cells (including eukaryotic and prokaryotic cells), viruses or virus particles, nucleic acids (including double stranded and single stranded DNA or RNA), plasmids, proteins, peptides, antibodies, enzymes, hormones, growth factors, carbohydrates and lipids, and derivatives, combinations or polymers thereof. A "biological material" according to the present invention may be a material of natural or of synthetic origin. A "biological material" may be extracted, recovered or obtained directly from a biological sample, such as, without limitation, blood, urine, cerebrospinal fluid, seminal fluid, saliva, sputum, stool, tissues or cells. In a preferred embodiment, biological material refers to nucleic acids.

"Biological reagent" refers to all reagents necessary to carry out a given biological or biochemical reaction. Examples of biological reagents include, but are not limited to, lysis reagents, amplification reagents, reverse-transcription reagents and the like.

"Lysis reagents" include, without limitation, proteinases (e.g., proteinase K, achromopeptidase, lysostaphin, etc.), salts (e.g., guanidinium thiocyanate, guanidinium hydrochloride, sodium thiocyanate, potassium thiocyanate, etc.), detergents (e.g., anionic detergents such as sodium dodecylsulphate (SDS); cationic detergent such as ethyltrimethylammonium bromide; non-ionic detergent such as Triton X-100, NP-40, Brij35, Tween 20, octyl glucoside, octyl thioglucoside, digitonin; zwitterionic detergents such as 3-[(3-cholamidopropyl)dimethylammonio]-1-propanesulfonate (CHAPS) and 3-[(3-cholamidopropyl)dimethylammonio]-2-hydroxy-1-propanesulfonate (CHAPSO)), buffers and the like.

"Amplification reagents" refers to all reagents necessary to carry out the amplification of a target nucleic acid sequence using PCR. Amplification reagents include, without limitation, oligonucleotide primers, DNA polymerase, a mix of 4 deoxyribonucleotides triphosphate (dNTPs) (namely deoxyadenosine triphosphate (dATP), deoxycytidine triphosphate (dCTP), deoxyguanosine triphosphate (dGTP) and (deoxy)thymidine triphosphate (dTTP)), salts, buffers and the like.

"Reverse-transcription reagents" include, without limitation, oligonucleotide primers, reverse transcriptase enzyme, a mix of 4 deoxyribonucleotides triphosphate (dNTPs) (namely deoxyadenosine triphosphate (dATP), deoxycytidine triphosphate (dCTP), deoxyguanosine triphosphate (dGTP) and (deoxy)thymidine triphosphate (dTTP)), salts, buffers and the like.

"Conductivity" and "electrical conductivity" are synonyms and refer to an intrinsic property of a given material which quantifies the intensity of the opposition of the material to the flow of electric charges. In the invention, the material is typically a liquid.

"Conductivity-improving compound" refers to a compound which increase the value of the conductivity of a composition when included in the composition, compared to another similar composition comprising the same ingredients, but wherein the conductivity-improving compound is not included.

"Emulsion" refers to a composition comprising at least two liquids, each of them being substantially immiscible in the other, wherein one of the liquid (which is referred to as the "dispersed phase") is partitioned into the other liquid (which is referred to as the "continuous phase"). Dispersed phase of an emulsion is typically suspended in the form of colloids, micelles, capsules and/or droplets. Dispersed phase and continuous phase are typically fully immiscible. Emulsions are typically stabilized by inclusion in the emulsion of one or more surfactants and/or emulsifying agents.

"Fluorinated oil" refers to an oil which contains at least one fluorine atom.

"Fluorinated surfactant" refers to a surfactant which contains at least one fluorine atom.

"Halogenated oil" refers to an oil which contains at least one halogen atom, such as fluorine (F), chlorine (Cl), bromine (Br), iodine (I), or astatine (At). Halogenated oils include fluorinated oils.

"Hydrophilic composition" refers to a composition which dissolve more readily in water than in oil or other non-polar organic solvents.

"Hydrophobic composition" refers to a composition which dissolve more readily in oil or other non-polar organic solvents than in water.

"Ionic compound" refers to a compound composed of ions held together by electrostatic forces, namely ionic bonding. The ionic compound is neutral overall, but consists of positively charged ions (cations) and negatively charged ions (anions). Examples of ionic compounds include salts and ionic liquids.

"Ionic liquid" refers to an ionic compound which is liquid below about 100° C. or to a salt with a melting point below about 100° C.

"Nucleic acid" refers to a polymer comprising ribonucleosides and/or deoxyribonucleosides that are covalently bonded, typically by phosphodiester linkages between subunits, but in some cases by phosphorothioates, methylphosphonates, and the like. Examples of nucleic acids include, but are not limited to, genomic DNA, circular DNA, low molecular weight DNA, plasmid DNA, circulating DNA, circulating tumor DNA (ctDNA), heterogeneous nuclear RNA (hnRNA), messenger RNA (mRNA), noncoding RNA (including ribosomal RNA (rRNA), transfer RNA (tRNA), micro RNA (miRNA), small interfering RNA (siRNA), small nucleolar RNA (snoRNA), small nuclear RNA (snRNA) and small temporal RNA (stRNA), fragmented or degraded nucleic acids, peptidic nucleic acids (PNAs), nucleic acid obtained from subcellular organelles such as mitochondria or chloroplasts, and nucleic acid obtained from microorganisms, parasites, or DNA or RNA viruses that may be present in a biological sample. Synthetic nucleic acid sequences that may or may not include nucleotide analogs that are added or "spiked" into a biological sample are also contemplated. In one embodiment, nucleic acid may be single-stranded, double-stranded, or double-stranded with single-stranded regions (e.g., stem- and loop- structures). Generally, nucleic acid can be extracted from a biological sample by a variety of techniques such as those described by Wood, E. J. (1983), *Molecular cloning: a laboratory manual* by Maniatis et al. Cold Spring Harbor Laboratory, New York. 1982.

"Oil" refers to a neutral, nonpolar chemical substance that is liquid at ambient temperature. Examples of oils are hydrocarbon oils, oxygenated oils, silicon oils or halogenated oils (including fluorinated oils).

"Oil-in-water emulsion" refers to an emulsion wherein the continuous phase is relatively more hydrophilic than the dispersed phase suspended therein, which is relatively more hydrophobic. Oil-in-water emulsions includes multiples emulsions such as for example water-in-oil-in-water emulsions and bi-liquid foam dispersions such as for example polyaphrons. In an oil-in-water emulsion according to the invention, dispersed phase is typically an oily phase. In an oil-in-water emulsion according to the invention, continuous phase is typically an aqueous phase.

"Oily composition" refers to a composition which comprises an oil.

"Oily phase" refers to a phase of an emulsion which comprises an oil. In the emulsion according to the invention, oily phase is typically more hydrophobic than the other phase of the emulsion, which is relatively more hydrophilic.

"Primer" or "oligonucleotide primer" refer to a single-stranded oligonucleotide, which is complementary to a target nucleic acid sequence and is capable of acting as a point for the initiation of synthesis of a primer extension product. In one embodiment, the primer is complementary to the sense strand of the target nucleic acid sequence and acts as a point of initiation for synthesis of a forward extension product, and is thereby termed "forward primer". In another embodiment, the primer is complementary to the antisense strand of the target nucleic acid sequence and acts as a point of initiation for synthesis of a reverse extension product, and is thereby termed "reverse primer". In one embodiment, amplification of nucleic acids requires pairs of primers, comprising forward and reverse primers. In one embodiment, one primer of a pair of primers binds at one end of the target nucleic acid sequence on one of the two paired DNA strands, and the other primer of the pair of primers binds at the opposite end of the target nucleic acid sequence on the other paired DNA strand.

"Solution" refers to a homogeneous mixture composed of two or more substances.

"Surfactant" refers to a substance that modifies the interfacial tension between two phases.

"Water-in-oil emulsion" refers to an emulsion wherein the continuous phase is relatively more hydrophobic than the dispersed phase suspended therein, which is relatively more hydrophilic. Water-in-oil emulsions includes multiples emulsions such as for example oil-in-water-in-oil emulsions and bi-liquid foam dispersions such as for example polyaphrons. In a water-in-oil emulsion according to the invention, dispersed phase is typically an aqueous phase. In a water-in-oil emulsion according to the invention, continuous phase is typically an oily phase.

DETAILED DESCRIPTION

The following Table 1 discloses the electrical conductivity of various liquids:

TABLE 1

| Liquid | Electrical conductivity |
| --- | --- |
| Mineral oil (hexadecane) | $<10^{-14}$ S/m |

TABLE 1-continued

| Liquid | Electrical conductivity |
|---|---|
| 3M ™ Fluorinert ™ FC-40 | $30 \times 10^{-15}$ S/m |
| 3M ™ Fluorinert ™ FC-770 | $33 \times 10^{-15}$ S/m |
| 3M ™ Fluorinert ™ FC-70 | $30 \times 10^{-15}$ S/m |
| Clearco Pure Silicone Fluids | $100 \times 10^{-15}$ S/m |
| 3M ™ Novec ™ HFE 7500 | $450 \times 10^{-9}$ S/m |
| Kerosene jet fuel | $5 \times 10^{-11}$ S/m |
| Deionized water | $6 \times 10^{-6}$ S/m |
| Drinking water | $5\text{-}50 \times 10^{-3}$ S/m |
| Salted water | 1-10 S/m |

As shown in Table 1, conductivity of pure oils such as mineral oils, silicone oils and fluorinated oils is very low, typically ranging from $10^{-13}$ to $10^{-15}$ S/m. This conductivity is 10 orders of magnitude below the lowest conductivity of an aqueous solution which is the conductivity of pure water: $6 \times 10^{-6}$ S/m.

Without being bound by any theory, the Applicant believe that the substantial difference between the conductivity of the dispersed phase and the conductivity of the continuous phase in an emulsion may be the cause of the electro-coalescence phenomena.

As described in detail in Example 1 below, the Applicant has evidenced a relation between increase of conductivity of continuous phase and reduction of electrocoalescence, so that including a conductivity-improving compound in the continuous phase may solve the technical problem of the electro-coalescence in emulsions.

The present invention relates to an emulsion comprising:
a continuous phase comprising a conductivity-improving compound,
a dispersed phase suspended in the continuous phase, and
a surfactant.

According to an embodiment, the emulsion is a water-in-oil or an oil-in-water emulsion. In an embodiment, the emulsion is a water-in-oil emulsion.

According to an embodiment, the emulsion comprises from 25 to 95% of the continuous phase, preferably from 35 to 95%, more preferably from 45 to 85%, furthermore preferably from 55 to 75%, in volume of the total volume of the emulsion (v/v). According to an embodiment, the emulsion comprises from 5 to 75% of the dispersed phase, preferably from 5 to 65% more preferably from 15 to 55%, furthermore preferably from 25 to 45%, in volume of the total volume of the emulsion (v/v).

According to an embodiment, the emulsion according to the invention is manufactured by any method known in the art, such as high shear mixing by means of magnetic stirrer, propeller or turbine stirrer, paddle device or whisk, homogenizer, colloid mill or ultrasound; membrane emulsification such as microfluidic methods (e.g. cross-flow, T-junction and flow focusing methods) or confinement gradient methods. According to an embodiment, the emulsion according to the invention is manufactured by a method according to the invention as described hereafter.

According to a first embodiment, the conductivity-improving compound is an oil. In an embodiment, the continuous phase comprises at least 75% of the conductivity-improving compound, preferably at least 80%, more preferably at least 85%, in volume of the total volume of the continuous phase (v/v). In an embodiment, the continuous phase is substantially free of any oil other than the conductivity-improving compound. In an embodiment, the continuous phase does not comprise any oil other than the conductivity-improving compound. In an embodiment, the continuous phase consists in the conductivity-improving compound and optionally the surfactant.

According to a second embodiment, the continuous phase comprises a conductivity-improving compound and an oil, such as for example hydrocarbon oils, oxygenated oils, silicon oils, halogenated oils, or mixtures thereof. In an embodiment, the continuous phase comprises at least 75% of the oil, preferably at least 80%, more preferably at least 85%, in volume of the total volume of the continuous phase (v/v). In an embodiment, the emulsion comprises a continuous oily phase comprising an oil and a conductivity-improving compound. In an embodiment, the emulsion comprises a continuous oily phase comprising a fluorinated oil and a conductivity-improving compound. In an embodiment, the emulsion comprises a continuous oily phase which is a solution comprising a fluorinated oil and a conductivity-improving compound. In an embodiment, the emulsion comprises a continuous oily phase comprising an oil and an ionic liquid, a dispersed aqueous phase suspended in the continuous oily phase, and a surfactant. In an embodiment, the emulsion comprises a continuous oily phase comprising a fluorinated oil and an ionic liquid, a dispersed aqueous phase suspended in the continuous oily phase, and a fluorinated surfactant. In an embodiment, the emulsion comprises a continuous oily phase which is a solution comprising a fluorinated oil and an ionic liquid, a dispersed aqueous phase suspended in the continuous oily phase, and a fluorinated surfactant. In an embodiment, the emulsion comprises a continuous oily phase comprising an oil and a conductivity-improving compound, a dispersed aqueous phase suspended in the continuous oily phase, and a surfactant. In an embodiment, the emulsion comprises a continuous oily phase comprising a fluorinated oil and a conductivity-improving compound, a dispersed aqueous phase suspended in the continuous oily phase, and a fluorinated surfactant.

In an embodiment, the emulsion comprises a continuous oily phase which is a solution comprising a fluorinated oil and a conductivity-improving compound, a dispersed aqueous phase suspended in the continuous oily phase, and a fluorinated surfactant.

In an embodiment, the oil is a fluorinated oil. In a specific embodiment, the fluorinated oil is selected from perfluoro-alkane such as perfluoro-hexane, perfluoro-cyclohexane, perfluoro-decaline; perfluoro-perhydrophenantrene; polyhexafluoropropylene oxide (e.g. Krytox™ oils) perfluoro polytrimethylene oxide (e.g. Denmum™ PFPEoils); poly perfluoroalkylene oxide (e.g. Solvay Galden® PFPE); perfluorotrialkylamines (e.g. 3M™ Fluorinert™ oils) such as N-bis(perfluorobutyl)N-trifluoromethyl amine (e.g. Fluorinert™ FC-40), tri(perfluoropentyl)amine (e.g. Fluorinert™ FC-70), mixture of perfluorooctane and perfluoro-1-oxacyclooctane amine (e.g. Fluorinert™ FC-77), perfluorotripropylamine (e.g. Fluorinert™ FC-3283); hydrofluoroethers (e.g. 3M™ Novec™ HFE oils) such as mixture of methyl nonafluorobutyl ether and methyl nonafluoroisobutyl ether (e.g. Novec™ HFE 7100), 3-ethoxy-1,1,1,2,3,4,4,5,5,6,6,6-dodecafluoro-2-(trifluoromethyl)-hexane (e.g. Novec™ 7500), 2,3,3,4,4-pentafluorotetrahydro-5-methoxy-2,5-bis [1,2,2,2-tetrafluoro-1-trifluoromethyl) ethyl]-furan (e.g. Novec™ HFE 7700); and mixtures thereof. In a further specific embodiment, the fluorinated oil is 3-ethoxy-1,1,1,2,3,4,4,5,5,6,6,6-dodecafluoro-2-(trifluoromethyl)-hexane (e.g. Novec™ HFE 7500).

In one embodiment, the dispersed phase is a hydrophilic composition. In one embodiment, the dispersed phase is an aqueous composition. In one embodiment, the dispersed phase is a hydrophobic composition.

In one embodiment, the dispersed phase comprises water and any water miscible co-solvent, such as for example ethers glycol and polyether glycols, dimethyl sulfoxide (DMSO), short organic alcohols, acetone, short fatty acids, glycerol, short organic amines, hydrogen peroxide, or organic and inorganic acids.

In one embodiment, the dispersed phase comprises water and reagents for performing a chemical and/or biological reaction. In one embodiment, the dispersed phase comprises water and chemical or biological reagents, buffers and/or catalysts required for a chemical and/or a biological reaction.

In one embodiment, the dispersed phase comprises biological material.

In one embodiment, the dispersed phase comprises reagents for PCR amplification of biological material. According to an embodiment, the dispersed phase comprises biological material. In an embodiment, the biological material is nucleic acids.

According to an embodiment, the surfactant is comprised in the continuous phase and/or in the dispersed phase. In an embodiment, the surfactant is comprised in the continuous phase. In an embodiment, the surfactant is a fluorinated surfactant, such as for example a fluorinated polymeric surfactant, fluorinated beads, fluorinated particles, beads with a fluorinated surface coating or particles with a fluorinated surface coating. In an embodiment, the fluorinated surfactant is selected from perfluoro-octanol; 1H,1H,2H,2H-perfluoro-1-octanol; perfluoro-decanol; 1H,1H,2H,2H-perfluoro-1-decanol; perfluoro-tetradecanoic acid; perfluoro-tetradecanoic oligo ethylene glycol; perfluoropolyether (PFPE) such as (PFPE)-COO$^-$, perfluoropolyether-polyethylene glycol (PFPE-PEG), perfluoropolyether-polyethylene glycol-perfluoropolyether (PFPE-PEG-PFPE), perfluoropolyether-dimorpholinophosphate (PFPE-DMP), polyhexafluoropropylene oxide carboxylate (PHFPO), polyhexafluoropropylene oxide-polyethylene glycol-polyhexafluoropropylene oxide (PHFPO-PEG-PHFPO), polyhexafluoropropylene oxide-polyether-polyhexafluoropropylene oxide (PHFPO-polyether-PHFPO); polyhexafluoropropylene oxide-polypropylene glycol-polyethylene glycol-polypropylene glycol-polyhexafluoropropylene oxide (PHFPO-PPG-PEG-PPG-PHFPO); and mixtures thereof. In a specific embodiment, the fluorinated surfactant is polyhexafluoropropylene oxide-polyethylene glycol-polyhexafluoropropylene oxide (PHFPO-PEG-PHFPO) copolymer. In another specific embodiment, the fluorinated surfactant is polyhexafluoropropylene oxide-polyether-polyhexafluoropropylene oxide. In another specific embodiment, the fluorinated surfactant is polyhexafluoropropylene oxide-polypropylene glycol-polyethylene glycol-polypropylene glycol-polyhexafluoropropylene oxide (PHFPO-PPG-PEG-PPG-PHFPO).

According to an embodiment, the concentration of the surfactant ranges from about 0.5 to about 30%, preferably from about 1 to about 10%, more preferably from about 3 to about 7%, most preferably is about 5%, in weight by total weight of the continuous phase (w/w).

In one embodiment, the concentration of the surfactant is about 0.5%, 1%, 2%, 3%, 4%, 5%, 6%, 7%, 8%, 9%, 10%, 12%, 14%, 16%, 18%, 20%, 25% or 30% in weight by total weight of the continuous phase (w/w).

According to another embodiment, the conductivity-improving compound also acts as a surfactant to stabilize the emulsion, so that the conductivity-improving compound is the surfactant. In an embodiment, the continuous phase does not comprise any surfactant other than the conductivity-improving compound.

According to an embodiment, the conductivity-improving compound is an ionic compound such as for example a salt. In one embodiment, the ionic compound comprises a hydrophobic cation and/or a hydrophobic anion. In an embodiment, the ionic compound comprises a fluorinated anion, such as for example bis(perfluoroalkylsulfonyl)imide wherein the perfluoroalkyl comprises from 1 to 8 carbon atoms, preferably from 1 to 4 carbon atoms, even more preferably 1 or 2 carbon atoms.

According to an embodiment, the conductivity-improving compound is an ionic liquid. In an embodiment, the ionic liquid comprises a hydrophobic cation and/or a hydrophobic anion. In an embodiment, the ionic liquid comprises a fluorinated anion and/or a fluorinated cation. In an embodiment, the ionic liquid comprises a fluorinated anion, such as for example bis(trifluoromethanesulfonyl)imide. In an embodiment, the ionic liquid comprises dialkylimidazolium, tetraalkylammonium, tetraalkylephosphonium, or alkylpyridium cations. In an embodiment, the ionic liquid comprises hexafluorophosphate, tetrafluoroborate, bis(trifluoromethanesulfonyl)imide, bis(pentafluoroethanesulfonyl)imide, tetracyanoborate, tris(pentafluoroethyl)trifluorophosphate, tosylate, or mesylate anions. In a specific embodiment, the ionic liquid is selected from N-trimethyl-N-butylammonium bis(trifluoromethanesulfonyl)imide, 1-butyl-1-methylpyrrolidinium bis(trifluoromethanesulfonyl)imide, 1-ethyl-3-methylimidazolium bis(trifluoromethylsulfonyl)imide, 1-hexyl-3-methyl imidazolium tris(pentafluoroethyl)trifluorophosphate, 2,3-dimethylimidazolium tetracyanoborate, N-tributyl-N-methylammonium bis(trifluoromethanesulfonyl)imide, and mixtures thereof.

In an embodiment, the ionic liquid is N-tributyl-N-methylammonium bis(trifluoromethanesulfonyl)imide.

According to an embodiment, the emulsion is biocompatible. According to an embodiment, the conductivity-improving compound is biocompatible.

In an embodiment, the biocompatible conductivity-improving compound is an ionic liquid comprising dialkylimidazolium, tetraalkylammonium, tetraalkylephosphonium, or alkylpyridium cations. In an embodiment, the biocompatible conductivity-improving compound is an ionic liquid comprising hexafluorophosphate, tetrafluoroborate, bistriflimide bis(trifluoromethanesulfonyl)imide, bis(pentafluoroethanesulfonyl)imide, tetracyanoborate, or tris(pentafluoroethyl) trifluorophosphate anions. In a specific embodiment, the biocompatible ionic liquid is selected from N-trimethyl-N-butylammonium bis(trifluoromethanesulfonyl)imide, 1-butyl-1-methylpyrrolidinium bis(trifluoromethanesulfonyl)imide, 1-ethyl-3-methylimidazolium bis(trifluoromethylsulfonyl)imide, 1-hexyl-3-methylimidazolium tris(pentafluoroethyl)trifluorophosphate, 2,3-dimethylimidazolium tetracyanoborate, N-tributyl-N-methylammonium bis(trifluoromethanesulfonyl)imide, and mixtures thereof.

In an embodiment, the biocompatible ionic liquid is N-tributyl-N-methylammonium bis(trifluoromethanesulfonyl)imide.

In one embodiment, the anion of the ionic liquid is not hexafluorophosphate. In one embodiment, the cation of the ionic liquid is not 1-butyl 3-methylimidazolium (also referred to as [BMIM$^+$]). In one embodiment, the ionic liquid is not 1-butyl 3-methylimidazolium hexafluorophosphate.

According to an embodiment, the conductivity-improving compound is more soluble in the continuous phase than in the dispersed phase. In an embodiment, the partition coefficient between continuous phase and dispersed phase $P_{C/D}$ (in volume) is such as log $P_{C/D}$ is at least 1, preferably at least 5, more preferably at least 10.

In one embodiment, the conductivity-improving compound is more soluble in oils, preferably in fluorinated oils, more preferably in hydrofluoroethers of low molecular weight. In other words, in one embodiment, the solubility of the conductivity-improving compound improves as the molecular weight of the oil, preferably the fluorinated oil, more preferably the hydrofluoroether, decreases. In still other words, in one embodiment, the solubility of the conductivity-improving compound improves as the boiling point of the oil, preferably the fluorinated oil, more preferably the hydrofluoroether, decreases.

In one embodiment, the solubility at 25° C. of the conductivity-improving compound ranges from about 0 to about 5 mol %, from about 0.25 to about 4.75 mol %, from about 0.5 to about 4.5 mol %, from about 1 to about 4 mol %, from about 1.5 to about 3.5 mol % in the oil, preferably in the fluorinated oil, more preferably in the hydrofluoroether. In one embodiment, the solubility at 25° C. of the conductivity-improving compound is about 0 mol %, 0.2 mol %, 0.4 mol %, 0.6 mol %, 0.8 mol %, 1.0 mol %, 1.1 mol %, 1.2 mol %, 1.3 mol %, 1.4 mol %, 1.5 mol %, 1.6 mol %, 1.7 mol %, 1.8 mol %, 1.9 mol %, 2.0 mol %, 2.1 mol %, 2.2 mol %, 2.3 mol %, 2.4 mol %, 2.5 mol %, 2.6 mol %, 2.7 mol %, 2.8 mol %, 2.9 mol %, 3.0 mol %, 3.1 mol %, 3.2 mol %, 3.3 mol %, 3.4 mol %, 3.5 mol %, 3.6 mol %, 3.7 mol %, 3.8 mol %, 3.9 mol %, 4.0 mol %, 4.2 mol %, 4.4 mol %, 4.6 mol %, 4.8 mol %, 5.0 mol % in the oil, preferably the fluorinated oil, more preferably the hydrofluoroether.

According to an embodiment, the conductivity-improving compound is entirely dissolved in the continuous phase. In one embodiment, the continuous phase is an oily phase comprising a fluorinated oil and a conductivity-improving compound and this continuous phase forms a solution (i.e. homogeneous mixture).

According to another embodiment, the conductivity-improving compound is partially insoluble in the continuous phase. In an embodiment, the partition coefficient between solubilized conductivity-improving compound and insoluble conductivity-improving compound. $P_{S/I}$ (in volume) is such as log $P_{S/I}$ ranges from −3 to 3, preferably from −2 to 2, more preferably from −1 to 1. In this embodiment, the continuous phase itself is an emulsion or a suspension of the conductivity-improving compound dispersed in the oil in the form of colloids, micelles, capsules or droplets. In an embodiment, immiscible part of the conductivity-improving compound is in liquid state, so that the continuous phase is an emulsion. In a specific embodiment, the emulsion of conductivity-improving compound is an emulsion wherein the mean droplet volume is lower than 0.2 pL, preferably lower than 0.02 pL, more preferably lower than 0.002 pL. This is advantageous because the colloids, micelles, capsules or droplets of conductivity-improving compound in a micro-emulsion are then too small to interfere with analytical methods such as ddPCR.

According to an embodiment, the concentration of the conductivity-improving compound is at least 0.01% in weight by total weight of the emulsion (w/w), preferably at least 0.02% w/w, at least 0.04% w/w, at least 0.06% w/w, at least 0.08% w/w, at least 0.1% w/w, at least 0.25% w/w, at least 0.5% w/w, at least 0.75% w/w, at least 1% w/w, at least 1.25% w/w, at least 1.5% w/w, at least 1.75% w/w, at least 2% w/w, at least 2.25% w/w, at least 2.5% w/w, at least 2.75% w/w, at least 3% w/w. According to an embodiment, the concentration of the conductivity-improving compound ranges from 0.1 to 40%, preferably from 0.5 to 20%, more preferably from 1 to 10%, more preferably from 3 to 10% in weight by total weight of the emulsion (w/w).

In one embodiment, the concentration of the conductivity-improving compound is about 0.01%, 0.02%, 0.04%, 0.06%, 0.08%, 0.1%, 0.25%, 0.5%, 0.75%, 1%, 1.25%, 1.5%, 1.75%, 2%, 2.25%, 2.5%, 2.75%, 3%, 4%, 5%, 6%, 7%, 8%, 9%, 10%, 12%, 14%, 16%, 18%, 20%, 25%, 30%, 35% or 40% in weight by total weight of the emulsion (w/w).

In an embodiment, the oil is a fluorinated oil, the surfactant is a fluorinated surfactant and the conductivity improving compound is an ionic liquid comprising a fluorinated anion and/or a fluorinated cation.

Advantageously, the continuous phase comprising the oil, the surfactant and the conductivity-improving compound have a conductivity which is $10^5$, preferably $10^{10}$, more preferably $10^{15}$ times higher than the conductivity of the mixture of the oil and the surfactant only.

The present invention also relates to a population of droplets comprising an aqueous phase, dispersed in a continuous oily phase comprising an oil and a conductivity-improving compound.

All features detailed above regarding the aqueous phase, the oily phase, the oil and the conductivity-improving compound also apply to the population of droplets.

In one embodiment, the population of droplets comprises an aqueous phase, dispersed in a continuous oily phase which is a solution comprising a fluorinated oil and a conductivity-improving compound.

In one embodiment, the conductivity-improving compound is present at a concentration such that coalescence between the droplets in the population of droplets is prevented.

In one embodiment, the conductivity-improving compound is present at a concentration such that the droplets in the population of droplets do not merge spontaneously.

According to an embodiment, the population of droplets is suspended in the continuous oily phase in the form of colloids, micelles, capsules and/or droplets. In an embodiment, the colloids, micelles, capsules, and/or droplets have a spherical shape.

According to an embodiment, the continuous oily phase contains a plurality of droplets of the population of droplets in a volume of the continuous oily phase. According to another embodiment, a volume of the continuous oily phase contains at least two distinct droplets of the population of droplets. This embodiment may be found within a "minimal" emulsion.

According to an embodiment, the droplets are in "contact", i.e., in close proximity one from the other while being separated by a thin (relatively to the average droplet size) film of the continuous oily phase. In one embodiment, "a thin film of the continuous oily phase", as used herein, means less than about ½ the radius of the droplets, preferably less than about ⅓, ¼, ⅕, ⅙, ⅐, ⅛, ⅑, 1/10, 1/15, 1/20 the radius of the droplets. According to another embodiment, the droplets are "at a distance" one from another, i.e., separated by a wide (relatively to the average droplet size) film of the continuous oily phase.

According to an embodiment, the population of droplets is monodispersed, i.e., that the standard deviation of distribution of the volumes of the droplets in the continuous oily phase is small (relatively to the average droplet volume). In an embodiment, the standard deviation of distribution of the volumes of the droplets in the emulsion is less than 50%, preferably less than 25%, more preferably less than 5%, furthermore preferably less than 1%, of the average droplet volume. This embodiment may be found within a "monodispersed" emulsion. According to another embodiment, the population of droplets is bi-dispersed, i.e., comprises two monodispersed population of droplets having a different average droplet volume. This embodiment may be found within a "bi-dispersed" emulsion. Similarly, the population of droplets may have three or more subpopulations of monodispersed populations of droplets.

According to another embodiment, the population of droplets is polydispersed, i.e., that the standard deviation of distribution of the volumes of the droplets in the continuous oily phase is strong (relatively to the average droplet volume).

According to one embodiment, the mean volume of the droplets ranges from about 0.0001 nL to about 100 nL, preferably from about 0.001 nL to about 10 nL, more preferably from about 0.01 nL to about 5 nL, more preferably from about 0.1 nL to about 2.5 nL.

According to one embodiment, the mean diameter of the droplets ranges from about 10 µm to about 200 µm, preferably from about 50 µm to about 150 µm, more preferably from about 75 µm to about 125 µm.

Local concentration is defined as aqueous phase/oily continuous phase volume ratio within a sphere centered at each droplet, the sphere having a diameter of ten times the mean diameter of the droplets. According to one embodiment, the local concentration in droplets is at least 30, preferably at least 40, more preferably at least 50.

According to an embodiment, each droplet in the population of droplets comprises biological material. In an embodiment, the biological material is a cell, a virus or a virus particle. In an embodiment, the biological material is nucleic acid.

According to an embodiment, each droplet in the population of droplets further comprises at least one pair of oligonucleotide primers being specific for a target nucleic acid sequence. In an embodiment, each droplet in the population of droplets further comprises a plurality of species of primer pairs, each species of primer pairs being specific for a different target nucleic acid sequence.

In one embodiment, each droplet in the population of droplets comprises a single nucleic acid template and a pair of oligonucleotide primers. In one embodiment, each droplet in the population of droplets comprises a single nucleic acid template and a plurality of species of primer pairs.

In one embodiment, the pair of oligonucleotide primers is specific for a target site of the single nucleic acid template.

In one embodiment, each primer pair of the plurality of species of primer pairs is specific for a different target site of the single nucleic acid template.

In an embodiment, each droplet in the population of droplets further comprises a plurality of species of detectable labels. In an embodiment, each species of detectable label hybridizes to a specific region in the target nucleic acid sequence.

In an embodiment, each droplet in the population of droplets further comprises reagents for carrying out an amplification reaction.

In one embodiment, the emulsion or the population of droplets according to the invention does not comprise tributyl phosphate (TBP).

The present invention also relates to a microfluidic device comprising:
a microchannel, and
a hydrophobic composition comprising an oil, a surfactant and a conductivity-improving compound in the microchannel.

The present invention also relates to a microfluidic device comprising:
a microchannel,
a hydrophobic composition comprising an oil, a surfactant and a conductivity-improving compound in the microchannel, and
a droplet generator means.

In one embodiment, a droplet generator means include, but is not limited to, a co-flow system, a flow focusing system, a T-junction system, a confinement gradient system (such as, e.g., that described in US patent application US2015267246), and a voltage-dependent system (such as, e.g., that described in US patent application US2011186784).

The present invention also relates to a microfluidic device comprising:
a microchannel,
a hydrophobic composition comprising an oil, a surfactant and a conductivity-improving compound in the microchannel,
a droplet generator means, and
at least two droplets, preferably a population of droplets, comprising an aqueous phase dispersed in said hydrophobic composition.

The present invention also relates to a microfluidic device comprising:
a microchannel,
a droplet generator means, and
an emulsion or population of droplets according to the present invention.

In one embodiment, the conductivity-improving compound is present at a concentration such that coalescence between the at least two droplets is prevented.

In one embodiment, the conductivity-improving compound is present at a concentration such that the at least two droplets do not merge spontaneously.

According to an embodiment, the dispersed phase is suspended in the continuous phase in the form of colloids, micelles, capsules, and/or droplets after injection. According to an embodiment, the hydrophilic composition is an aqueous composition. According to an embodiment, the hydrophobic composition is an oily composition. According to an embodiment, the conductivity-improving compound is an ionic liquid.

According to an embodiment, the hydrophilic composition is suitable for containing biological material without degradation of the biological material. In an embodiment, the biological material is nucleic acids.

An example of microfluidic chip according to the present invention is the microfluidic chip disclosed in European patent EP2903738. Another example of microfluidic chip according to the present invention is the Sapphire chip (Stilla Technologies).

The present invention also relates to a kit comprising a microfluidic chip according to the invention and a container comprising an aqueous composition as described herein above.

According to an embodiment, the hydrophilic composition is an aqueous composition. According to an embodiment, the hydrophilic composition is biocompatible and/or suitable for containing biological material without degradation of the biological material. In an embodiment, the biological material is nucleic acids.

The present invention also relates to a process for manufacturing an emulsion according to the invention, comprising a step of mixing together a hydrophilic composition and a hydrophobic composition comprising a conductivity-improving compound, in presence of a surfactant comprised in the hydrophilic composition or in the hydrophobic composition.

According to an embodiment, the hydrophilic composition is mixed in the hydrophobic composition in the form of colloids, micelles, capsules, and/or droplets. According to an embodiment, the hydrophilic composition is an aqueous composition. According to an embodiment, the hydrophobic composition is an oily composition. According to an embodiment, the conductivity-improving compound is an ionic liquid. In an embodiment, the hydrophobic composition is an oily composition comprising an oil, an ionic liquid, and a surfactant.

According to an embodiment, the step of mixing of the hydrophilic composition and the hydrophobic composition is performed in a microfluidic chip.

According to an embodiment, the hydrophilic composition comprises biological material, preferably nucleic acids. In an embodiment, the biological material is nucleic acids.

The present invention also provides methods for analyzing biological material. In one embodiment, the biological material is analyzed in the emulsion of the invention.

The present invention also provides methods for forming biological material droplets, processing biological material and/or detecting biological material. In one embodiment, the present invention provides methods for digital processing and/or detection of biological material in the emulsion of the invention. In one embodiment, the present invention provides methods for digital processing and/or detection of biological material in the droplets of the invention.

Droplet-based microfluidic systems have been shown to be compatible with many chemical and biological reagents and capable of performing a variety of "digital fluidic" processes that can be rendered programmable and reconfigurable. A number of methods for performing biological reactions in an emulsion have been described and are implemented with or using commercially available products (e.g., Teh et al., Lab Chip. 2008 February; 8(2):198-220).

In one embodiment, the dispersed phase of the emulsion according to the present invention comprises biological material. In one embodiment, the continuous phase of the emulsion according to the present invention comprises biological material.

In one embodiment, the biological material is selected from the group consisting of organisms, organs, tissues, cells (including eukaryotic and prokaryotic cells), viruses or virus particles, nucleic acids (including double stranded and single stranded DNA or RNA), plasmids, proteins, peptides, antibodies, enzymes, hormones, growth factors, carbohydrates and lipids, and derivatives, combinations or polymers thereof. In a preferred embodiment, the biological material is a cell, a virus or a virus particle. In a preferred embodiment, the biological material is nucleic acid.

Methods for processing and/or detecting nucleic acids in emulsions are described in the art. In international patent application WO1999002671, Tawfik and Griffiths describe the expression of nucleic acids in the droplet compartments of an emulsion, as well as the amplification of nucleic acids in the droplet compartments.

In one embodiment, the methods of the invention involve:
forming an emulsion according to the present invention comprising a biological material, preferably the biological material is in the dispersed phase of the emulsion of the invention, more preferably the biological material is in droplets,
processing said biological material in the emulsion of the invention, preferably in droplets, and
detecting said biological material in the emulsion of the invention, preferably in droplets.

In one embodiment, the methods of the invention involve:
partitioning the dispersed phase of the emulsion of the invention into droplets, wherein the dispersed phase comprises a biological material,
processing said biological material in the emulsion of the invention, preferably in droplets, and
detecting said biological material in the emulsion of the invention, preferably in droplets.

It is advantageous when implementing such methods that the droplets within the emulsion do not coalesce. Hence, using the emulsion of the present invention, wherein the continuous phase comprises a conductivity-improving compound that renders the emulsion less sensitive to electrocoalescence, is advantageous.

In one embodiment, the methods of the present invention are carried out in a microfluidic chip according to the present invention.

The methods of the present invention include forming an emulsion or a population of droplets according to the present invention, comprising a biological material. In one embodiment, the biological material is in the dispersed phase of the emulsion, preferably the biological material is in droplets.

In one embodiment, the methods of the present invention include partitioning the dispersed phase of the emulsion into droplets. In one embodiment, the dispersed phase comprises biological material.

In one embodiment, the methods of the present invention include flowing the dispersed phase through a droplet generator means, preferably through the droplet generator means of a microfluidic device according to the present invention, into a continuous phase comprising a conductivity-improving compound.

In one embodiment, the emulsion according to the present invention is a one-dimensional emulsion (i.e., the dispersed phase forms a one-dimensional population of droplets in which each droplet in the emulsion is touching a maximum of 2 other droplets), a two-dimensional emulsion (i.e., the dispersed phase forms a two-dimensional population of droplets in which each droplet in the emulsion is touching a maximum of 8 other droplets) or a three-dimensional emulsion (i.e., the dispersed phase of the emulsion forms a three-dimensional population of droplets in which each droplet in the emulsion is touching a maximum of 26 other droplets). In an embodiment, the emulsion is a one-dimensional emulsion or a two-dimensional emulsion. In a specific embodiment, the emulsion is a two-dimensional emulsion.

In one embodiment, the methods include forming an emulsion or a population of droplets comprising cells. In one embodiment, the cells are in the dispersed phase of the emulsion, preferably the cells are in droplets.

In one embodiment, some droplets do not contain any cell to be further processed and/or detected. In one embodiment, some droplets contain a single cell to be further processed and/or detected. In one embodiment, some droplets contain more than one cell to be further processed and/or detected. In a preferred embodiment, at least a fraction of the droplets within the emulsion or the population of droplets comprises a single cell to be further processed and/or detected.

In one embodiment, the methods include forming an emulsion or a population of droplets comprising a nucleic acid template. In one embodiment, the nucleic acid template is in the dispersed phase of the emulsion, preferably the nucleic acid template is in droplets. In one embodiment, some droplets do not contain any nucleic acid template to be further processed and/or detected. In one embodiment, some droplets contain a single nucleic acid template to be further processed and/or detected. In one embodiment, some droplets contain more than one nucleic acid template to be further processed and/or detected. In a preferred embodiment, at least a fraction of the droplets within the emulsion or the population of droplets comprises a single nucleic acid template to be further processed and/or detected.

In a preferred embodiment, the distribution of cells or nucleic acid template within the droplets of the emulsion or of the population of droplets obeys the Poisson distribution.

However, methods for non-Poisson loading of droplets are known to those familiar with the art.

In one embodiment, the dispersed phase typically comprises an aqueous buffer solution, such as ultrapure water (e.g., 18 MΩ resistivity), TE buffer (10 mM Tris HCl and 1 mM EDTA), phosphate buffer saline (PBS) or acetate buffer. Any liquid or buffer that is biocompatible with biological material, in particular with cells and/or nucleic acids, can be used.

In one embodiment, the aqueous phase of the emulsion or of the population of droplets further comprises biological reagents for processing biological material. Advantageously, the emulsion, preferably the aqueous phase of the emulsion, and/or the conductivity-improving compound, do not inhibit biological reactions such as lysis, amplification, reverse transcription and the like; and/or do not interact with detectable labels used for detecting biological material in droplets.

The methods of the present invention include processing biological material in droplets. By "processing biological material" is meant performing a biological and/or chemical reaction on the biological material, including, without limitation, reactions of lysis, amplification, reverse-transcription and the like.

In one embodiment, the methods of the present invention involve lysing cells in the emulsion or in the population of droplets of the present invention, preferably in the dispersed phase of the emulsion, more preferably in droplets.

Lysis refers to the disruption of a cell by breaking its cellular membrane, in order to gain access to biological material that is otherwise inaccessible. Lysis methods are well-known to the skilled artisan, and include, but are not limited to, proteolytic lysis, chemical lysis, thermal lysis, mechanical lysis, and osmotic lysis.

Upon cell lysis, the content of the cell (e.g., its nucleic acids such as genomic DNA, messenger RNAs and the like) is released within the droplet and becomes accessible for further processing in the droplet.

In one embodiment, the methods of the present invention involve reverse transcribing nucleic acids in the emulsion or in the population of droplets of the present invention, preferably in the dispersed phase of the emulsion, more preferably in droplets.

Reverse transcription refers to the replication of RNA (such as, e.g., messenger RNAs released upon cell lysis) using a RNA-directed DNA polymerase (also called reverse transcriptase, RT) to produce complementary strands of DNA (cDNA). The reverse-transcription of RNAs may be carried out by techniques well known to the skilled artisan, using a reverse transcriptase enzyme and a mix of 4 deoxyribonucleotides triphosphate (dNTPs), namely deoxyadenosine triphosphate (dATP), deoxycytidine triphosphate (dCTP), deoxyguanosine triphosphate (dGTP) and (deoxy) thymidine triphosphate (dTTP).

In some embodiments, the reverse-transcription of RNAs comprises a first step of first-strand cDNA synthesis. Methods for first-strand cDNA synthesis are well-known to the skilled artisan. First-strand cDNA synthesis reactions can use a combination of sequence-specific primers, oligo(dT) primers or random primers. Examples of reverse transcriptase enzymes include, but are not limited to, M-MLV reverse transcriptase, SuperScript II (Invitrogen), SuperScript III (Invitrogen), SuperScript IV (Invitrogen), Maxima (ThermoFisher Scientific), ProtoScript II (New England Biolabs) and PrimeScript (ClonTech).

In one embodiment, the methods of the present invention involve amplifying a nucleic acid template in the emulsion or in the population of droplets of the present invention, preferably in the dispersed phase of the emulsion, more preferably in droplets.

Amplification refers to production of additional copies of a nucleic acid template and is generally carried out using polymerase chain reaction (PCR) or other technologies well known in the art. Techniques to amplify nucleic acid include specific amplification methods as well as random amplification methods. Specific amplification methods include, but are not limited to, methods requiring thermal cycling (such as PCR, nested PCR, ligase chain reaction, ligase detection reaction, transcription-mediated amplification (TMA)) and/or isothermal amplification systems (such as self-sustaining sequence replication, replicase system, helicase system, strand displacement amplification (SDA), nucleic acid sequence-based amplification (NASBA), rolling circle amplification (RCA), and hyperbranched rolling circle amplification (HRCA)). Random amplification techniques include, without limitation, multiple displacement amplification (MDA), random PCR, random amplification of polymorphic DNA (RAPD) and multiple annealing and looping based amplification cycles (MALBAC).

In one embodiment, amplification of a nucleic acid template is carried out by polymerase chain reaction (PCR) or a variant thereof. PCR refers to methods by Mullis (U.S. Pat. Nos. 4,683,195 and 4,683,202) for increasing concentration of a nucleic acid template sequence in a mixture of nucleic acids, without cloning or purification. Variants of PCR include, but are not limited to, allele-specific PCR, asymmetric PCR, crystal digital PCR, digital PCR, digital droplet PCR, hot-start PCR, intersequence-specific PCR, methylation-specific PCR, miniprimer PCR, multiplex ligation-dependent probe amplification, multiplex-PCR, nested PCR, quantitative PCR, reverse transcription PCR and/or touchdown PCR.

The process for amplifying a nucleic acid template includes introducing amplification reagents to a nucleic acid mixture containing a desired nucleic acid template, followed by a sequence of thermal cycling.

To effect amplification, oligonucleotide primers are annealed to their complementary sequence within the nucleic acid template. The primer may occur naturally, as in a purified restriction digest, or be produced synthetically. In one embodiment, the length of a primer ranges from about 5 to about 200 nucleotides, from about 5 to about 100 nucleotides, from about 5 to about 75 nucleotides, from about 5 to about 50 nucleotides, from about 10 to about 35 nucleotides, or from about 18 to about 22 nucleotides. In one embodiment, the primer does not comprise the exact sequence of the nucleic acid template. In one embodiment, the primer is sufficiently complementary to hybridize with the nucleic acid template for primer elongation to occur, i.e., the primer is sufficiently complementary to the nucleic acid template such that the primer will anneal to the nucleic acid template under conditions that permit primer extension. As used herein, the terms "conditions that permit primer extension" refers to those conditions, e.g., salt concentration, pH, temperature, and necessary cofactor concentration, among others, under which a given polymerase enzyme catalyzes the extension of an annealed primer. Conditions for the primer extension activity of a wide range of polymerase enzymes are known in the art.

Primers can be prepared by a variety of methods including, but not limited to, cloning of appropriate sequences and direct chemical synthesis using methods well known in the art. Primers can also be obtained from commercial sources.

DNA polymerases suitable to amplify nucleic acids comprise, but are not limited to, Taq polymerase Stoffel fragment, Taq polymerase, Advantage DNA polymerase, AmpliTaq, AmpliTaq Gold, Titanium Taq polymerase, KlenTaq DNA polymerase, Platinum Taq polymerase, Accuprime Taq polymerase, Pfu polymerase, Pfu polymerase turbo, Vent polymerase, Vent exo-polymerase, Pwo polymerase, 9 Nm DNA polymerase, Therminator, Pfx DNA polymerase, Expand DNA polymerase, rTth DNA polymerase, DyNAzyme-EXT Polymerase, Klenow fragment, DNA polymerase I, T7 polymerase, Sequenase, Tfi polymerase, T4 DNA polymerase, Bst polymerase, Bca polymerase, phi-29 DNA polymerase and DNA polymerase Beta or modified versions thereof.

In a preferred embodiment, amplification of a nucleic acid template is carried out in the emulsion of the present invention, preferably in the dispersed phase of the emulsion, more preferably in droplets. Methods for amplifying a nucleic acid template in droplets include, but are not limited to, digital PCR (dPCR), droplet digital PCR (ddPCR), crystal digital PCR, digital retro-transcriptase PCR (digital RT-PCR), digital expression of a nucleic acid and digital protein expression.

The methods of the present invention include detecting biological material in the emulsion of the present invention, preferably in the dispersed phase of the emulsion, more preferably in droplets. By "detecting biological material" is meant assessing the presence or absence and/or quantifying the amount of biological material, e.g., using detectable labels. In a preferred embodiment, the methods of the present invention include detecting nucleic acids in the emulsion of the present invention, preferably in the dispersed phase of the emulsion, more preferably in droplets. In one embodiment, the methods of the present invention include detecting nucleic acids amplified upon amplification in the emulsion of the present invention, preferably in the dispersed phase of the emulsion, more preferably in droplets.

Detectable labels include optically-labeled probes such as fluorescently-labeled probes. Examples of fluorescent labels include, but are not limited to, Atto dyes; 4-acetamido-4'-isothiocyanatostilbene-2,2' disulfonic acid; acridine and derivatives thereof (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; brilliant yellow; coumarin and derivatives thereof (e.g., 7-amino-4-methylcoumarin [also named AMC or coumarin 120], 7-amino-4-trifluoromethylcoumarin [also named coumarin 151] and 7-diethylamino-3-(4'-isothiocyanatophenyl)-4-methylcoumarin); cyanine dyes; cyanosine; 4',6-diaminidino-2-phenylindole (DAPI); 5'5''-dibromopyrogallol-sulfonaphthalein (also named bromopyrogallol red); diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin, erythrosin and derivatives thereof (e.g., eosin isothiocyanate, erythrosin B and erythrosin isothiocyanate); ethidium; fluorescein and derivatives thereof (e.g., 5-carboxyfluorescein [FAM], 5-(4,6-dichlorotriazin-2-yl)aminofluorescein [DTAF], 2',7'-dimethoxy-4'5'-dichloro-6-carboxyfluorescein, fluorescein isothiocyanate [FITC], quinolizinofluorescein isothiocyanate [QFITC])); fluorescamine; IR144; IR1446; malachite green isothiocyanate; 4-methylumbelliferoneortho cresolphthalein; nitrotyrosine; pararosaniline; phenol red; B-phycoerythrin; o-phthaldialdehyde; pyrene and derivatives thereof (e.g., pyrene butyrate and succinimidyl 1-pyrene); butyrate quantum dots; reactive red 4 (also named Cibacron™ brilliant red 3B-A); rhodamine and derivatives thereof (e.g., 6-carboxy-X-rhodamine [ROX], 6-carboxyrhodamine [R6G], lissamine rhodamine B sulfonyl chloride rhodamine [Rhod], rhodamine B, rhodamine 123, rhodamine X isothiocyanate, sulforhodamine B, sulforhodamine 101, sulfonyl chloride derivative of sulforhodamine 101 [Texas Red], N,N,N',N'-tetramethyl-6-carboxyrhodamine [TAMRA], tetramethyl rhodamine, and tetramethyl rhodamine isothiocyanate [TRITC]); riboflavin; rosolic acid; terbium chelate derivatives; Cy3; Cy5; Cy5.5; Cy7; IRD 700; IRD 800; La Jolta Blue; phthalo cyanine; and naphthalo cyanine. Labels other than fluorescent labels are contemplated by the invention, including other optically-detectable labels.

In one embodiment, the droplets of the invention contain a plurality of detectable probes that hybridize to the biological material, e.g., to the nucleic acids, in droplets. Members of the plurality of probes can each include the same detectable label, or a different detectable label. The plurality of probes can also include one or more groups of probes at varying concentration. The groups of probes at varying concentrations can include the same detectable label which vary in intensity, due to varying probe concentrations.

The number of droplets largely defines the precision and resolution of the nucleic acid detection, where an increase in the number of droplets improves precision and therefore enables resolution of small concentration differences between nucleic acid sequences in a sample.

In one embodiment, the detection occurs by the scanning a monolayer of droplets (i.e., a one-dimensional or a two-dimensional network of droplets) confined in a storage device, preferably in a detection area of the microfluidic chip of the invention. Droplets stored in this fashion can be scanned either by the movement of the microfluidic chip by the scanner or the movement of the scanner over the microfluidic chip.

EXAMPLES

The present invention is further illustrated by the following examples.

Example 1: Emulsions without Conductivity-Improving Compound

The Applicant has studied the occurrence and intensity of electro-coalescence in emulsions of a given aqueous phase (a PCR mix, hereafter named Aqueous Phase A) and two different continuous phases (hereafter named Oily Phase 1 and Oily Phase 2).

As showed in Table 2 below, FC-40 and Novec-7500 are two fluorinated oil presenting very similar physical properties. The only physical property for which the difference between the oils is higher than the order of magnitude is the electrical conductivity: the electrical conductivity of Novec-7500 is more than a million times higher than that of FC-40.

TABLE 2

|  | Novec-7500 | FC-40 |
| --- | --- | --- |
| Boiling point (° C.) | 128 | 155 |
| Melting point (° C.) | −100 | −57 |
| Molecular weight (g/mol) | 414 | 650 |
| Critical Temperature (° C.) | 261 | 270 |
| Critical Pressure (MPa) | 1.55 | 1.18 |
| Vapor Pressure (kPa) | 2.1 | 0.43 |
| Heat of Vaporization (kj/kg) | 89 | 68 |
| Liquid Density (kg/m3) | 1614 | 1850 |
| Coefficient of Expansion (/K) | 0.0013 | 0.0012 |
| Kinematic Viscosity (cSt) | 0.77 | 1.8 |
| Absolute Viscosity (cP) | 1.24 | 3.4 |
| Specific Heat (J/kg-K) | 1128 | 1100 |
| Thermal Conductivity (W/m-K) | 0.0065 | 0.065 |
| Surface Tension (mN/m) | 16.2 | 16 |
| Solubility in Water (ppm by weight) | <3 | <5 |
| Dielectric Strength, 0.1" gap (kV) | ~40 | >40 |
| Dielectric Constant @ 1 kHz | 5.8 | 1.9 |
| Electrical conductivity (S/m) | $45 \times 10^{-8}$ | $25 \times 10^{-15}$ |

Behavior of two water-in-oil emulsions having two different continuous phases was studied.

Materials and Methods

Aqueous Phase A was manufactured by diluting in Nuclease-Free water:
20% v/v Perfecta PCR Toughmix Mastermix 5x (from Quantaboisciences, USA),
fluorescein sodium salt (100 nM final concentration),
PCR primers (final concentration 500 nM), and
FAM-labelled probes to amplify and detect in Blue epifluorescence the gene that encodes for the protein BRAF in human genomic DNA (final concentration 250 nM).

Various quantity of human genomic DNA (200 to 400 copies per microliter) was then added depending on the experiment.

Oily Phase 1 was manufactured by diluting 5% w/w of fluorinated surfactant polyhexafluoropropylene oxide-polyethylene glycol-polyhexafluoropropylene oxide (PHFPO-PEG-PHFPO) in fluorinated oil 3-ethoxy-1,1,1,2,3,4,4,5,5,6,6,6-dodecafluoro-2-(trifluoromethyl)-hexane (3M™ Novec™ 7500). PHFPO-PEG-PHFPO is described in European patent application EP2315629 (in particular in Example 1, reaction 2), which is hereby entirely incorporated by reference.

Oily Phase 2 was manufactured by diluting 5% w/w of fluorinated surfactant polyhexafluoropropylene oxide-polyethylene glycol-polyhexafluoropropylene oxide (PHFPO-PEG-PHFPO) in fluorinated oil N-bis(perfluorobutyl)N-trifluoromethyl amine (3M™ Fluorinert™ FC 40).

Two Sapphire chip (from Stilla Technologies SAS, France) were each loaded with 123 µL of oily Phase 1 or of oily Phase 2.

25 µL of aqueous Phase A was pipetted in the inlet port of each chip. A difference of pressure between the inlet and the outlet port was applied on each chip in order to produce two-dimensional water-in-oil emulsions of droplets within the chip. The aqueous Phase A constituted the discontinuous phase and the oily Phase 1 or 2 constituted the continuous phase of these emulsion.

A thermal treatment (1—heating up to 95° C. for 5 minutes; 2—45 cycles of 95° C. for 30 seconds and 58° C. for 15 seconds; 3—cooling down to 25° C.) was then applied to the emulsions to activate the PCR reaction in the dispersed phases. Each of the chip was then loaded into an inverted epifluorescence microscope (Prism3—Stilla Technologies, France) and microscope images were recorded.

After imaging, each of the chip was taken out of the microscope and rubbed with a nitrile laboratory glove, in order to simulate experimental manipulation of the Sapphire chips which is known to cause electrocoalescence. Each of the chip was then loaded back into the microscope and microscope images were recorded.

Results

Figure 1:
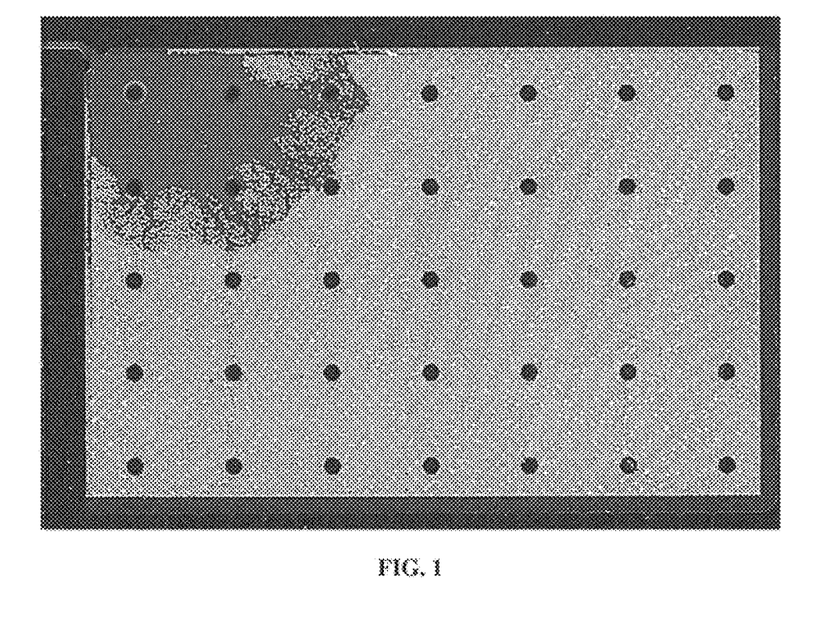
FIG. 1 is a photograph showing an epifluorescence imaging of an emulsion with Phase 1 as a continuous phase immediately after emulsification and thermic treatment.
Figure 3:
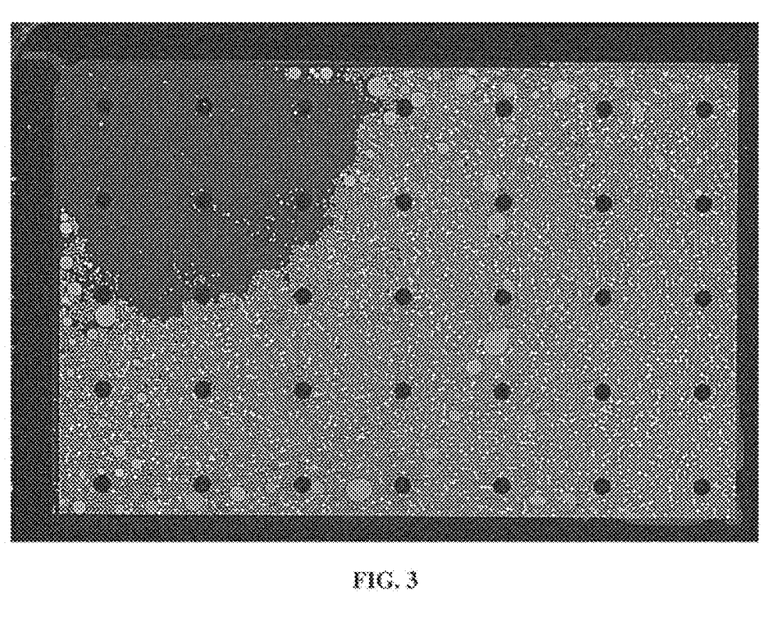
FIG. 3 is a photograph showing an epifluorescence imaging of an emulsion with Phase 2 as a continuous phase immediately after emulsification and thermic treatment.

The microscope images of the emulsions before rubbing for the experiments using the oily Phases 1 and 2 are displayed respectively in FIG. 1 and FIG. 3.

As shown in FIG. 1, the emulsion comprising oily Phase 1 withstood thermal treatment for PCR amplification and was suitable for subsequently imaging. By contrast, as shown in FIG. 3, the emulsion comprising the oily Phase 2 displayed large regions of coalesced droplets, indicating that previous electro-coalescence events took place within the emulsion.

Figure 2:
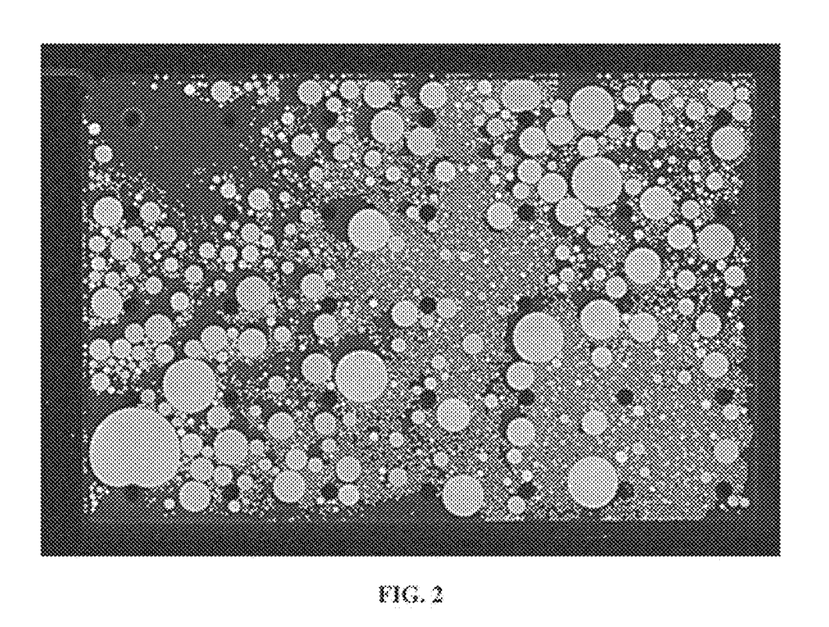
FIG. 2 is a photograph showing an epifluorescence imaging of an emulsion with Phase 1 as a continuous phase after rubbing with a lab glove.
Figure 4:
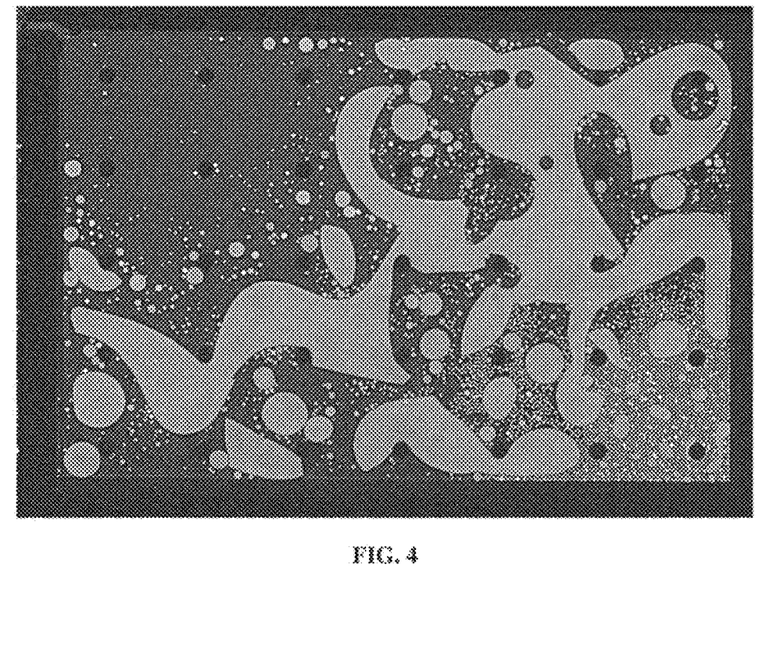
FIG. 4 is a photograph showing an epifluorescence imaging of an emulsion with Phase 2 as a continuous phase after rubbing with a lab glove.

The microscope images of the emulsions after rubbing for the experiments using the emulsions comprising oily Phase 1 and 2 are displayed respectively in FIG. 2 and FIG. 4.

As shown in FIG. 2, the emulsion comprising oily Phase 1 displayed many large droplets due to electrocoalescence. However, it was still suitable for quantify DNA by digital PCR. By contrast, as shown in FIG. 4, the emulsion comprising oily Phase 2 had almost totally coalesced into a few large droplets, and could no more be used for quantifying DNA by digital PCR.

This experiment thus evidences the technical problem of the sensitivity of emulsions to electrocoalescence, to be solved within the present invention.

Conclusion

The experiments thus showed that:
1. The occurrence frequency of electro-coalescence events under a given electrical forcing is higher in the emulsion wherein the continuous phase is FC-40.

2. The threshold of the intensity of the electrical forcing required to induce an electro-coalescence event is lower in the emulsion wherein the continuous phase is FC-40.
3. The scale of an electro-coalescence event, i.e. the number of droplets that coalescence during an electro-coalescence event, is higher in the emulsion wherein the continuous phase is FC-40.

In conclusion, the emulsion wherein the continuous phase (Novec-7500) has a relatively higher electrical conductivity is less sensitive to electro-coalescence than an emulsion wherein the continuous phase (FC-40) has a relatively lower electrical conductivity.

Therefore, the reduction of sensitivity for emulsions with highly conductive continuous phases is apparent through three parameters: (1) the occurrence frequency of electro-coalescence events under a given stimulation decreases as the electrical conductivity of the continuous phase increases; (2) the threshold of the intensity of the stimulation required to induce electro-coalescence events can occur increases as the electrical conductivity of the continuous phase increases; (3) the scale of an electro-coalescence event decreases as the electrical conductivity of the continuous phase increases.

Example 2: Emulsion with Conductivity-Improving Compound

Materials and Methods

Oily Phase 3 was manufactured by diluting 5% w/w of fluorinated surfactant polyhexafluoropropylene oxide-polyethylene glycol-polyhexafluoropropylene oxide (PHFPO-PEG-PHFPO) and 5% w/w of ionic liquid N-tributyl-N-methylammonium bis(trifluoromethanesulfonyl)imide (99.5% purity from Solvionics, France), in fluorinated oil 3-ethoxy-1,1,1,2,3,4,4,5,5,6,6,6-dodecafluoro-2-(trifluoromethyl)-hexane (3M™ Novec™ 7500). Oily Phase 3 was thus equivalent to oily Phase 1 wherein a conductivity-improving compound had been added.

A two-dimensional emulsion of aqueous Phase A in oily Phase 3 is manufactured within a Sapphire Chip in the conditions described in Example 1. A thermal treatment, imaging, rubbing and imaging were applied to this emulsion as described in Example 1.

Results

Figure 5:
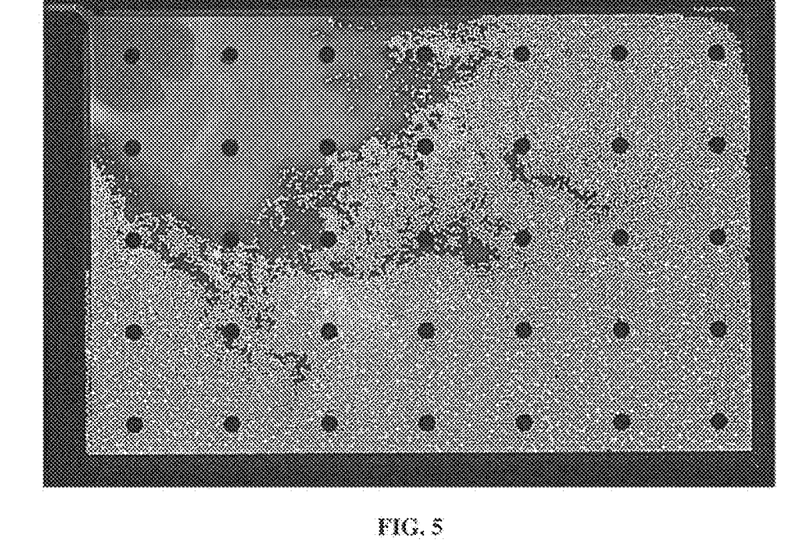
FIG. 5 is a photograph showing an epifluorescence imaging of an emulsion with Phase 3 as a continuous phase immediately after emulsification and thermic treatment.

The microscope images of the emulsions before rubbing for the experiments using the oily Phase 1 (of Example 1) and oily Phase 3 are displayed respectively in FIG. 1 and FIG. 5.

FIG. 1 and FIG. 5 show than in both cases, the emulsions were sufficient stable to withstand thermal treatment for PCR amplification and to be subsequently imaged. The presence of the ionic liquid as conductivity-improving compound at 6% v/v in the oily Phase 3 did not destabilize the emulsion compared to the emulsion comprising oily Phase 1 which did not comprise the conductivity-improving compound.

Figure 6:
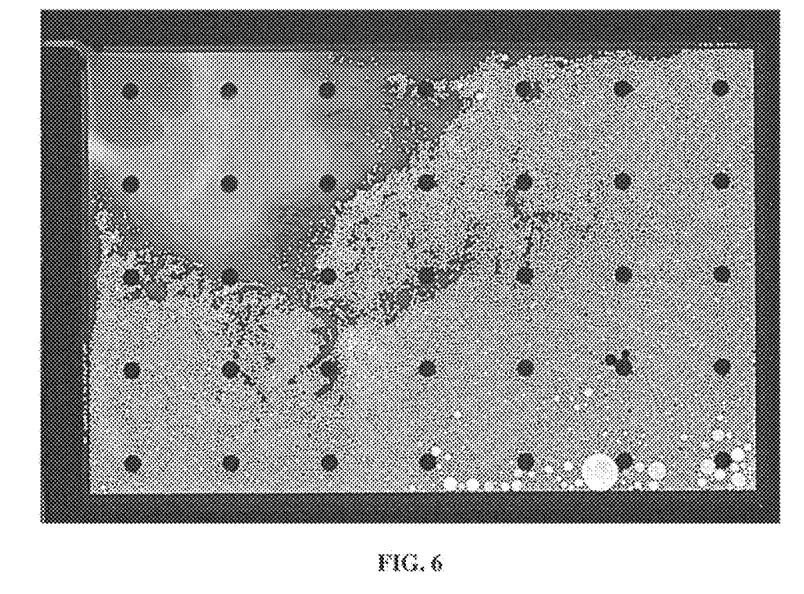
FIG. 6 is a photograph showing an epifluorescence imaging of an emulsion with Phase 3 as a continuous phase after rubbing with a lab glove.

The microscope images of the emulsions after rubbing for the experiments using the emulsions comprising oily Phase 1 and 2 are displayed respectively in FIG. 2 and FIG. 6.

As shown in FIG. 2 and FIG. 6, the emulsion comprising oily Phase 3 was almost not affected by rubbing and electro-coalescence as it displayed only a few small coalesced droplets, whereas the emulsion comprising oily Phase 1 displayed many large coalesced droplets. Emulsion comprising oily Phase 3

This experiment evidences that the presence in the continuous phase of an emulsion of a conductivity-improving compound, such as an ionic liquid, significantly reduce the sensitivity of the emulsion to electrocoalescence.

Example 3: ddPRC Assay

Materials and Methods

The ability to quantify DNA by digital PCR using emulsions comprising the oily Phases 1, 2 and 3 (of Examples 1 and 2) was measured using Sapphire Chips primed each with one of the oily Phases 1, 2 and 3 and by running a digital PCR assay on the Naica System, a digital PCR system provided by Stilla Technologies.

To quantify DNA by digital PCR, an emulsion was formed inside the Sapphire Chip using the aqueous phase of Example 1 as dispersed phase and one of the oily Phase 1, 2 or 3 as the continuous phase.

The Sapphire Chips underwent a thermal treatment using the Naica Geode instrument of the Naica System to induce PCR amplification of the DNA targets in the emulsion and were subsequently imaged using the Naica Prism3 instrument.

In the fluorescence images, droplets having a strong fluorescent signal after thermocycling are droplets that initially contained at least one amplifiable target DNA in each of them. These droplets are called positive droplets. Droplets having a low fluorescent signal are droplets that initially did not contain an amplifiable target DNA. These droplets are called negative droplets.

Consequently, the initial amount of DNA target in the aqueous solution can be measured by counting the number of positive and negative partitions in the images and applying a statistical correction.

Image analysis and DNA quantification is automatically performed using the Crystal Miner software from Stilla Technologies for the experiments using emulsions comprising the oily Phases 1, 2 and 3.

Results

Following Table 3 shows the results of the analysis.

TABLE 3

| Continuous oily phase | | Analyzable droplets | Lost droplets after rubbing | DNA quantification (copies/µL) | Incertitude coefficient |
|---|---|---|---|---|---|
| Phase 1 | Before rubbing | 26557 | — | 336.0 | 3.2% |
| | After rubbing | 5061 | 21496 (81%) | 353.6 | 7.3% |
| Phase 2 | Before rubbing | 18808 | — | 235.1 | 4.8% |
| | After rubbing | 1065 | 17743 (94%) | 251.5 | 19% |
| Phase 3 | Before rubbing | 18336 | — | 328.7 | 3.8% |
| | After rubbing | 17831 | 505 (2.8%) | 331.7 | 3.8% |

Using emulsions comprising oily Phases 1 and 2, rubbing leads to a loss of 80% to nearly 95% of analyzable droplets, leading to a significant increase (from twice to 4-times) in the uncertainty coefficient of the DNA quantification.

For the emulsion comprising the oily Phase 3, rubbing only leads to a loss of 3% of the total analyzable droplets, with insignificant effects on the uncertainty of the measurement.

This experiment evidences that the presence of conductivity-improving compound, such as an ionic liquid, does not inhibit PCR amplification within the droplets while successfully preventing electro-coalescence of the emulsion during handling of the Sapphire Chip.

The invention claimed is:

1. An emulsion comprising:
   a continuous oily phase which is a solution comprising a fluorinated oil and a conductivity-improving compound, wherein said conductivity-improving compound is an ionic liquid,
   a dispersed aqueous phase dispersed in said continuous oily phase, and
   a fluorinated surfactant.

2. The emulsion according to claim 1, wherein said fluorinated surfactant is selected from the group consisting of perfluoro-octanol; 1H,1H,2H,2H-perfluoro-1-octanol; perfluoro-decanol; 1H,1H,2H,2H-perfluoro-1-decanol; perfluoro-tetradecanoic acid; perfluoro-tetradecanoic oligo ethylene glycol; perfluoropolyether; perfluoropolyether-polyethylene glycol; perfluoropolyether-polyethylene glycol-perfluoropolyether; perfluoropolyether-dimorpholinophosphate; polyhexafluoropropylene oxide carboxylate; polyhexafluoropropylene oxide-polyethylene glycol-polyhexafluoropropylene oxide; polyhexafluoropropylene oxide-polyether-polyhexafluoropropylene oxide; polyhexafluoropropylene oxide-polypropylene glycol-polyethylene glycol-polypropylene glycol-polyhexafluoropropylene oxide and mixtures thereof.

3. The emulsion according to claim 1, wherein said fluorinated oil is selected from the group consisting of perfluoro-hexane; perfluoro-cyclohexane; perfluoro-decaline; perfluoro-perhydrophenantrene; poly-hexafluoropropylene oxide; perfluoro polytrimethylene ether; poly perfluoroalkylene oxide; fluorinated amines, tri(perfluoropentyl)amine, mixture of perfluorooctane amine and perfluoro-1-oxacyclooctane amine, perfluorotripropylamine; fluorinated ethers, 3-ethoxy-1,1,1,2,3,4,4,5,5,6,6,6-dodecafluoro-2-(trifluoromethyl)-hexane, 2,3,3,4,4-pentafluorotetrahydro-5-methoxy-2,5-bis[1,2,2,2-tetrafluoro-1-trifluoromethyl) ethyl]-furan; and mixtures thereof.

4. The emulsion according to claim 1, wherein said ionic liquid comprises a fluorinated anion, a fluorinated cation, or a mixture thereof.

5. The emulsion according to claim 1, wherein said ionic liquid is selected from the group consisting of N-trimethyl-N-butylammonium bis(trifluoromethanesulfonyl)imide, 1-butyl-1-methylpyrrolidinium bis(trifluoromethanesulfonyl)imide, 1-ethyl-3-methylimidazolium bis(trifluoromethylsulfonyl)imide, 1-hexyl-3-methylimidazolium tris(pentafluoroethyl)trifluorophosphate, 2,3-dimethylimidazolium tetracyanoborate, N-tributyl-N-methylammonium bis(trifluoromethanesulfonyl)imide, and mixtures thereof.

6. The emulsion according to claim 1, wherein said ionic liquid is N-tributyl-N-methylammonium bis(trifluoromethanesulfonyl)imide.

7. The emulsion according to claim 1, wherein said aqueous phase comprises biological material, reagents, or a mixture thereof for performing a chemical reaction, a biological reaction, or a chemical and biological reaction.

8. A microfluidic device comprising:
   a microchannel,
   a droplet generator means, and
   the emulsion according to claim 1 in the microchannel.

9. A method for analyzing a biological material, comprising:
   forming the emulsion according to claim 1, the emulsion comprising a biological material;
   processing said biological material in said emulsion, and
   detecting said biological material in said emulsion.

10. The method according to claim 9, wherein said biological material is cells or nucleic acids.

11. The method according to claim 9, wherein the step of processing of the biological material comprises amplifying the biological material.

12. The method according to claim 11, wherein the step of processing of the biological material comprises amplifying the biological material by PCR.

13. The method according to claim 11, wherein the step of processing of the biological material comprises amplifying the biological material by droplet digital PCR (ddPCR).

14. The emulsion according to claim 1, wherein said ionic liquid comprises bis(trifluoromethanesulfonyl)imide.

15. The emulsion according to claim 7, wherein said biological material is a nucleic acid template.

16. The emulsion according to claim 3, wherein said poly-hexafluoropropylene oxide is a poly-hexafluoropropylene oxide with carboxylic end group; or said fluorinated amine is N-bis(perfluorobutyl)N-trifluoromethyl amine; or said fluorinated ethers is a mixture of methyl nonafluorobutyl ether and methyl nonafluoroisobutyl ether.

* * * * *